United States Patent [19]

Häberle et al.

[11] Patent Number: 4,977,183

[45] Date of Patent: Dec. 11, 1990

[54] 3-HALOSUCCINIMIDES AND PLANT FUNGICIDAL USE THEREOF

[75] Inventors: Norman Häberle, Munich; Anneliese Reutter, Eglharting, both of Fed. Rep. of Germany

[73] Assignee: The Dow Chemical Company, Midland, Mich.

[21] Appl. No.: 406,404

[22] Filed: Sep. 12, 1989

Related U.S. Application Data

[62] Division of Ser. No. 240,763, Jun. 15, 1988, Pat. No. 4,900,840.

[51] Int. Cl.$^5$ .................. A01N 37/32; C07D 207/404
[52] U.S. Cl. ..................................... 514/425; 548/545
[58] Field of Search .......................... 548/545; 514/425

[56] References Cited

FOREIGN PATENT DOCUMENTS

88/02747 4/1988 European Pat. Off. ............ 548/545

3636552 5/1988 Fed. Rep. of Germany ...... 548/545

Primary Examiner—David B. Springer
Attorney, Agent, or Firm—S. Preston Jones; Ronald G. Brookens

[57] ABSTRACT

The invention concerns fungicidal compounds of the formula

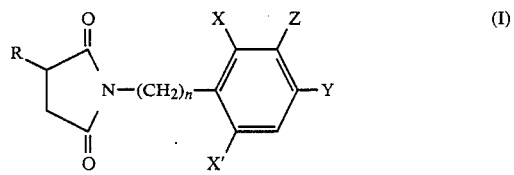

wherein R signifies a chlorine, bromine or iodine atom, n 0, 1, 2 or 3 and X, X', Y and Z have the meanings given in the description.

7 Claims, No Drawings

3-HALOSUCCINIMIDES AND PLANT FUNGICIDAL USE THEREOF

This is a divisional of Ser. No. 240,763, filed Jun. 15, 1988 now U.S. Pat. No. 4,900,880.

The invention concerns certain N-substituted 3-halosuccinimides, a process for their preparation, as well as the use of these compounds as fungicidal-active materials.

In DE-AS 20 12 656 and in JP Kokai 75 129 743 are described some N-substituted 3-halosuccinimides as fungicidal-active materials.

It was the task of the invention to prepare new substances with high fungicidal effectiveness. A further task of the present invention was to make available fungicidal-active substances with wide activity spectrum. In particular, it was the task of the present invention to prepare substances which still show satisfectory effectivenesses against fungus strains in which a substantial resistance towards N-(3,5-dichlorophenyl)-substituted dicarboximides is present. Furthermore, it was, in particular, the task of the present invention to make available fungicidal substances which show good effectivenesses not only against Botrytis cinerea but also against the types of fungus frequently accompanying this fungus, such as for example Alternaria types or Penicillium types.

In the scope of the present invention, these tasks were solved in that compounds of the formula

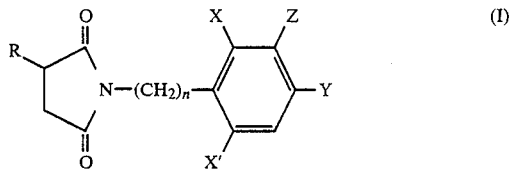

were synthesised, wherein R signifies a chlorine, bromine or iodine atom, n 0, 1, 2 or 3, X, X' and Z each the same or different residues, namely, hydrogen atoms, fluorine atoms or methyl groups and Y a hydrogen, fluorine, chlorine or bromine atom or a methyl group, with the proviso that for n=0 and at the same time R=Cl, at least one of the residues X, X', Y and Z is not a hydrogen atom and that when Z does not signify a hydrogen atom, at least one of the residues X, X' and Y also does not signify a hydrogen atom.

Preferred are compounds of the formulae

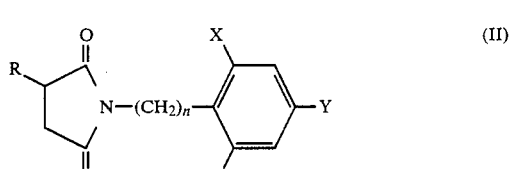

and

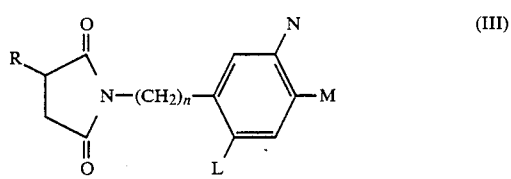

wherein R, n, X, Y have the same meanings as for formula (I), whereby the residues X are, in each case, the same residues and L and N signify the same or different residues, namely, methyl groups or fluorine atoms, and M signifies a hydrogen atom or a methyl group.

Especially preferred because of their fungicidal effectiveness are those compounds of the formulae (II) and (III) for which R signifies a bromine atom, especially those of the formula

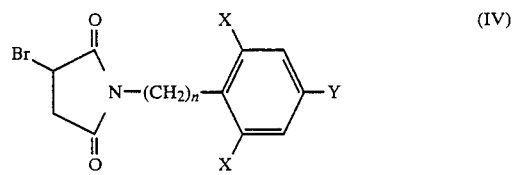

wherein n, X and Y have the meanings given for formula (I), whereby the residues X are, in each case, the same residues.

In formula (IV), the residues X preferably each signify two hydrogen atoms or two methyl groups.

Because of its especially high fungicidal effectiveness, the compound of the formula

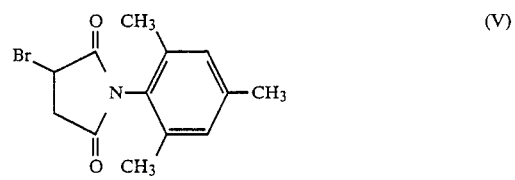

is especially preferred.

The 3-halosuccinimides of formula (I) according to the invention are optically active because of a centre of asymmetry on the carbon atom in 3-position on the heterocycle. It is entirely possible that one of the enantiomers in question (3-R- or 3-S-enantiomer) contributes more strongly than the other to the desired action. By the expression "compounds of the formula" are, in every case, to be understood the optically pure 3-R- or 3-S-enantiomers, as well as all mixtures of at least one 3-R- with at least one 3-S-isomer, for example the corresponding racemates.

The compounds according to the invention are, for example, preparable as follows:

1. By reaction of compounds of the formula

with those of the formula

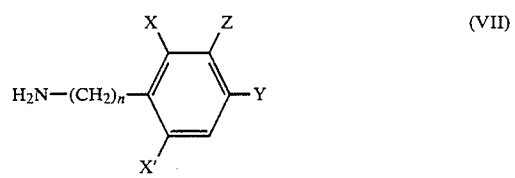

to give the corresponding hemi-amides and ring closure in the presence of agents promoting the condensation, for example acetyl chloride;

2. By reaction of compounds of the formula

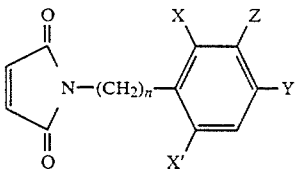 (VIII)

(preparable according to 1. from maleic acid anhydride and compounds of the formula (VII) with hydrogen halides of the formula HR in a suitable solvent, for example trichloromethane.

3. It is especially advantageous when, for the preparation of compounds of the formula (I) according to the invention, compounds of the formula

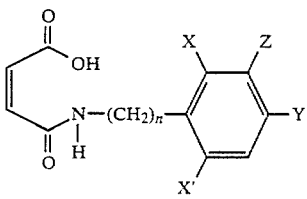 (IX)

are reacted with those of the formula

CH₃COR' (X)

whereby R, n, X, X', Y and Z have the meanings given in claim 1 and R' signifies a chlorine or bromine atom, and, if R signifies an iodine atom, the so obtained product of the formula

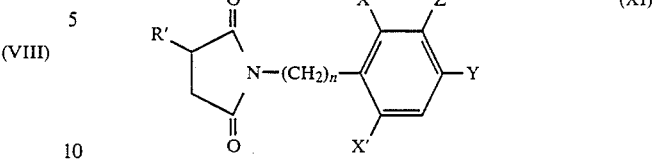 (XI)

is subsequently reacted in per se known manner with alkali metal iodide, preferably sodium iodide, preferably in a suitable solvent, such as acetone.

Because of the sensitivity of 3-iodosuccinimides towards oxidation and dehydrohalogenation, it is fundamentally of advantage to prepare the 3-iodosuccinimides according to the invention in the above-described way from the corresponding 3-chloro or 3-bromo derivatives.

The succinic acid amides of the formula (IX) are obtainable by the reaction of compounds of the formula (VII) with succinic acid anhydride. The amines of the formula (VII) needed as starting materials are commercially available or can be prepared in known manner.

According to the above-described methods, there were prepared the compounds set out in the following Tab. 1. However, the present invention is in no way limited to these materials.

TABLE 1

| active material No. | chemical designation | sum formula | melting point in °C. |
|---|---|---|---|
| 1 | 3-chloro-1-(2,4,6-trimethyl-phenyl)-2,5-pyrrolidinedione | $C_{13}H_{14}ClNO_2$ | 125 |
| 2 | 3-bromo-1-(4-fluorophenyl)-2,5-pyrrolidinedione | $C_{10}H_7BrFNO_2$ | 154 |
| 3 | 3-bromo-1-(4-methylphenyl)-2,5-pyrrolidinedione | $C_{11}H_{10}BrNO_2$ | 163 |
| 4 | 3-bromo-1-(2,6-difluorophenyl)-2,5-pyrrolidinedione | $C_{10}H_6F_2NO_2$ | oil |
| 5 | 3-bromo-1-(5-fluoro-2-methyl-phenyl)-2,5-pyrrolidinedione | $C_{11}H_9BrFNO_2$ | 121 |
| 6 | 3-bromo-1-(2-fluoro-5-methyl-phenyl)-2,5-pyrrolidinedione | $C_{11}H_9BrFNO_2$ | 96 |
| 7 | 3-bromo-1-(2,4,6-trimethyl-phenyl)-2,5-pyrrolidinedione | $C_{13}H_{14}BrNO_2$ | 131 |
| 8 | 3-bromo-1-(4-bromo-2,6-dimethyl-phenyl)-2,5-pyrrolidinedione | $C_{12}H_{11}Br_2NO_2$ | 122 |
| 9 | 3-bromo-1-(2,4-dimethyl-5-fluorophenyl)-2,5-pyrrolidinedione | $C_{10}H_{11}BrFNO_2$ | 115 |
| 10 | 3-bromo-1-(phenylethyl)-2,5-pyrrolidinedione | $C_{12}H_{12}BrNO_2$ | 81 |
| 11 | 3-bromo-1-(phenylpropyl)-2,5-pyrrolidinedione | $C_{13}H_{14}BrNO_2$ | oil |
| 12 | 3-bromo-1-(4-methylphenyl)-ethyl-2,5-pyrrolidinedione | $C_{13}H_{14}BrNO_2$ | 66 |
| 13 | 3-bromo-1-(4-chlorophenyl)-ethyl-2,5-pyrrolidinedione | $C_{12}H_{11}BrClNO_2$ | 96 |
| 14 | 3-iodo-1-(4-methylphenyl)-2,5-pyrrolidinedione | $C_{11}H_{10}INO_2$ | 159 |
| 15 | 3-iodo-1-(4-fluorophenyl)-2,5-pyrrolidinedione | $C_{10}H_7FINO_2$ | 118 |
| 16 | 3-iodo-1-(2,4,6-trimethyl-phenyl)-2,5-pyrrolidinedione | $C_{13}H_{14}INO_2$ | 160 |

The compounds according to the invention display fungitoxic properties. They are used against fungal attack in plants or on plant products.

They prove, for example, to be highly effective against all living forms of Botrytis cinerea and against their accompanying fungi, such as Alternaria solani and Penicillium glaucum. It is to be especially emphasised that the active materials according to the invention are also effective against those Botrytis strains which already show appearances of resistance against known dicarboxanilides, the common feature of which is a 3,5-dichlorophenyl radical present on an imide nitrogen.

Furthermore, those fungi are combated such as Alternaria types, Septoria types, *Verticillium dahliae*, Colletotrichum types, Monilia types, Fusarium types and Oomycetes, such as e.g. *Pythium ultimum*.

The active materials according to the invention are characterised by a broad spectrum of activity. Thus, for example, not only is Botrytis combated but also the typical accompanying fungi. Consequently, with the active material according to the invention, there can be treated the whole complex of fungal diseases and thus the increased growth of accompanying fungi often observed in the case of unilateral treatment can be prevented.

Without their field of use being limited thereto, the active materials are suitable e.g. for use in viticulture, in horticulture, especially in salad cultivations or in nursery plants (alpine violets, geraniums), in ornamental lawns, in hop crops, in rape crops, in strawberry cultivations and in stoned fruit plantations.

The application of the active materials takes place in per se known manner in the living area of the fungi, for example by pouring, splashing, spraying, dusting, coating. There can thereby be achieved not only a prophylactic but also a curative action.

The active materials according to the invention can be applied alone or in admixture with other pesticides, especially fungicidal agents. In general, they are used as mixtures with solid or liquid dilution agents or as solutions in solid or liquid solvents, with active material contents of 0.005 to 95 wt. %.

In general, the mixtures of solutions are produced as emulsion concentrates, pastes, spray powders, granulates or microcapsules.

In general, emulsion concentrates and pastes contain 10 to 90 wt. %, preferably 15 to 50 wt. % of active material, 2 to 25 wt. % of dispersion adjuvant materials and organic solvents and/or water.

Spray powders mostly contain 10 to 80 wt. %, preferably 15 to 70 wt. % of active material, 1 to 30 wt. % of dispersion adjuvant materials and 10 to 89 wt. % of inert components.

Granulates and microcapsules contain, besides inert components and/or coating materials, 1 to 10 wt. %, preferably 5 to 10 wt. % of active material.

There are used according to the invention: as dispersion adjuvant materials, e.g. alkyl and aryl sulphonates, methyl cellulose, polymeric sulphonic acids and their salts, polyalcohols, fatty acid esters, fatty alcohol ethers, fatty amines;

as organic solvents, e.g. alcohols, such as ethanol, butanols, dimethylformamide, dimethyl sulphoxide, N-methylpyrrolidione, aromatics, such as toluene and xylenes;

as inert components, e.g. kaolin, China clay, talc, calcium carbonate, highly dispersed silicic acid, silica gel, kieselguhr, diatomaceous earth, pumice, brick dust, coarse-ground maize, thickening agents, such as starch and carboxymethylcellulose, cyclodextrins;

as binding agents, e.g. magnesium sulphate, gypsum, gum arabic, polyvinyl alcohol.

For use as fungicides, the active materials according to the invention are formulated, for example, as follows:

Spray powder 20 wt. % active material
44 wt. % China clay
16 wt. % highly dispersed silicic acid
15 wt. % lignin sulphonate (cell pitch)
5 wt. % sodium alkylnaphthalenesulphonate-formaldehyde condensate (Atlox 4862, Registered Trade Mark, manufacturer: Atlas-Chemie, D-4300 Essen)

Emulsion Concentrate 20 wt. % active material
30 wt. % cyclohexanone
30 wt. % xylene
20 wt. % Tween Twenty (Registered Trade Mark, manufacturer Atlas-Chemie, D-4300 Essen).

The following Examples serve for the explanation of the invention. The products according to the invention were, in each case, identified by $^1$H-NMR.

EXAMPLE 1: PREPARATION EXAMPLE

3-Bromo-1-(4-fluorophenyl)-2,5-pyrrolidinedione, active material 2

29.4 g. (0.3 mole) maleic acid anhydride were dissolved in 300 ml. toluene and a solution of 33.3 g. (0.3 mole) 4-fluoroaniline in 100 ml. toluene added thereto at 30° C. The hemi-anilide rapidly precipitated out. For the completion of the reaction, the mixture was heated for 2 hours to 100° C., then cooled, the precipitated product filtered off, washed and dried. The yield of hemi-anilide was quantitative. The hemianilide was suspended in acetic acid ethyl ester and 43 g. (0.35 mole) acetyl bromide added thereto. The reaction was carried out by stirring at 30° C. (2 hrs.) and by subsequent 2 hours heating to reflux, thereafter the solvent was distilled off and the residue crystallised. The yield amounted to 69.2 g. (corresponding to 85.5% of theory). The product displayed a melting point of 154° C.

NMR (in CDCl$_3$ as solvent, tetramethylsilane as inner standard): 2.9–3.8 ppm (4 doublets, J=3 or 9 Hz; ring CH$_2$), 4.8 or 4.95 (2 doublets, J=3 Hz; ring CH), 7.0–7.45 (multiplet, 4 aromat. protons) in the ratio of 2:1:4.

EXAMPLE 2, PREPARATION EXAMPLE

3-Iodo-1-(4-fluorophenyl)-2,5-pyrrolidinedione, active material 15

27.2 g. (0.1 mole) of the 3-bromo-1-(4-fluorophenyl)-2,5-pyrrolidinedione prepared according to Example 1 were dissolved in 140 ml. acetone and a solution of 15.75 g. (0.105 mole) sodium iodide in acetone added thereto. The mixture was stirred for 2 hours at room temperature and then heated to reflux for 1 hour. Subsequently, it was cooled, filtered off from resultant sodium bromide and the filtrate evaporated. The residue was recrystallised from methanol/water (3:1) and gave the desired product with 70.5% of theory. The melting point of the derivative lay at 118° C.

EXAMPLE 3, PREPARATION EXAMPLE

3-Bromo-1-(2,4-dimethyl-5-fluorophenyl)-2,5-pyrrolidinedione, active material 9

13.9 g. (0.1 mole) 2,4-dimethyl-5-fluoroaniline and 9.8 g. (0.1 mole) maleic acid anhydride were reacted with one another as described in Example 1. The yield amounted to 70.2% of theory; the melting point of the product lay at 115° C.

Preparation of the starting material (according to B. C. Becker and R. Adams, J. Am. chem. Soc. 54, 2980 (1932): 60.5 g. commercially available 2,4-dimethylaniline were slowly added at 0°–10° C. to 340 ml. conc. sulphuric acid and 72.5 ml. conc. nitric acid (D=1.4) added dropwise thereto in the course of one hour, while stirring, also at 0°–10° C. Subsequently, it was further stirred for 30 min., the mixture then poured on to ice and the precipitate diazotised with 35 g. sodium nitrite at 0°–10° C. in about 2.5 hrs. After a further 30 min. stirring, 88 ml. 50% aqueous $HBF_4$ were added dropwise thereto at 0° C., stirred for a further 30 min. and then the separated precipitate filtered off (52.5 g. after washing and drying). This product was now decomposed portionwise in the course of 5 hrs. at 130° C. and distilled ($bp_{12}$ 103° C.). The yield amounted to 14.8 g. (corresponding to 17.4% of theory).

This nitro compound was now dissolved in 125 ml. methanol and hydrogenated with $PtO_2$ as catalyst with hydrogen at 35°–45° C. (exothermal reaction) in the course of 3 hrs. After filtering, evaporating and crystallising, there were obtained 11 g. (corresponding to 93% of theory) of the desired aniline derivative. Melting point of the amine 58°–60° C.

EXAMPLE 4, PREPARATION EXAMPLE

3-Bromo-1-(4-chlorophenyl)-ethyl-2,5-pyrrolidinedione, active material 13

9.8 g. (0.1 mole) maleic acid anhydride were dissolved in 100 ml. toluene and a solution of 15.6 g. (0.1 mole) commercially available 2-(4-chlorophenyl)-ethylamine in toluene added thereto at 30° C. The maleic acid hemi-amide rapidly precipitated out. After a further two hours, the hemi-amide was filtered off (m.p. 136°–138° C.). Subsequently, it was suspended in acetic acid ethyl ester, 12.9 g. (0.105 mole) acetyl bromide added thereto and the mixture heated, while stirring, for 2 h. to 30°–40° C., whereby the precipitate gradually dissolved. Thereafter, it was heated under reflux for a further 2 hours, the solvent then stripped off and the residue crystallised. The product can be recrystallised from ethanol and then melts at 96° C. The yield amounts to 78.0% by theory.

For the following working examples, from the known state of the art there were chosen three especially similar substances as comparative agents. These are:

1. 3-bromo-1-(3,5-dichlorophenyl)-2,5-pyrrolidinedione, known from DE 2.012.656, in the following referred to as "comparison A", 2. 3-chloro-1-(2,4,6-trimethylphenyl)-1H-pyrrol-2,5-dione, known from FR 2,226,396, in the following referred to as "comparison B", 3. 3-chloromethyl-1-(2,4,6-trimethylphenyl)-2,5-pyrrolidinedione, known from EPA No. 0,173.284, in the following referred to as "comparison C".

EXAMPLE 5, WORKING EXAMPLE

Spore Germination Test

50 μl. of a solution or suspension of an active material with a content of 250 or 16 ppm of active substance were placed into the hollow cut-out of a hollow cut-out object carrier, together with 50 μl. of a spore suspension prepared by slurrying the spores of an agar culture with a solution which, per liter, contained 10 g. sugar, 1 g. glycol, 1 g. $KH_2PO_4$ and 0.5 g. $MgSO_4$. The object carriers were kept at 20° C. for 48 hours in a Petri dish, the bottom of which was covered with moist filter paper.

Thereafter, the ratio of the germinated and of the non-germinated spores was compared against an untreated control sample.

The degree of working is given in % according to the following formula:

$$100 - \frac{\text{number of germinated spores, treated}}{\text{number of germinated spores, untreated}} \times 100$$

The results are summarised in the following Tab. 2 and 3.

TABLE 2

| | Fungitoxicity of 2,5-pyrrolidinediones according to the invention at 250 ppm active material concentraion in % | | | | | | |
|---|---|---|---|---|---|---|---|
| Active material | Alternaria solani | Botrytis cinerea | Fusarium culmorum | Fusarium nivale | Colletotrichum coffeanum | Verticillium dahliae | Penicillium glaucum |
| 1 | 100 | 80 | 100 | 100 | 100 | 100 | 80 |
| 2 | 100 | 100 | 100 | 100 | 100 | 100 | 70 |
| 3 | 40 | 100 | 100 | 100 | 100 | 100 | 60 |
| 4 | 100 | 100 | 100 | 100 | 100 | 100 | 100 |
| 5 | 100 | 100 | 100 | 100 | 100 | 100 | 100 |
| 6 | 100 | 100 | 100 | 100 | 100 | 100 | 100 |
| 7 | 100 | 100 | 100 | 100 | 100 | 100 | 100 |
| 8 | 100 | 100 | 100 | 100 | 100 | 100 | 100 |
| 9 | 100 | 100 | 95 | 100 | 100 | 100 | 95 |
| 10 | 100 | 100 | 100 | 100 | 100 | 100 | 100 |
| 11 | 100 | 80 | 100 | 100 | 100 | 100 | 100 |
| 12 | 100 | 100 | 90 | 100 | 100 | 100 | 100 |
| 13 | 100 | 100 | 100 | 100 | 100 | 100 | 10 |
| 14 | 80 | 100 | 100 | 100 | 100 | 100 | 0 |
| 15 | 100 | 100 | 100 | 100 | 100 | 100 | 100 |
| 16 | 100 | 100 | 100 | 100 | 100 | 100 | 100 |

TABLE 3

| | Fungitoxicity of 2,5-pyrrolidinediones and of comparative substances at 16 ppm active material concentration | | | | | | |
|---|---|---|---|---|---|---|---|
| Active material | Alternaria solani | Botrytis cineria | Fusarium culmorum | Fusarium nivale | Colletorichum coffeanum | Verticillium dahliae | Penicillium glaucum |
| 1 | 100 | 30 | 20 | 100 | 100 | 80 | 0 |

TABLE 3-continued

Fungitoxicity of 2,5-pyrrolidinediones and of comparative substances at 16 ppm active material concentration

| Active material | Alternaria solani | Botrytis cineria | Fusarium culmorum | Fusarium nivale | Colletorichum coffeanum | Verticillium dahliae | Penicillium glaucum |
|---|---|---|---|---|---|---|---|
| 3 | 30 | 100 | 40 | 100 | 100 | 80 | 0 |
| 7 | 100 | 80 | 90 | 100 | 100 | 100 | 80 |
| 8 | 100 | 80 | 100 | 100 | 100 | 100 | 75 |
| 13 | 100 | 85 | 70 | 100 | 100 | 100 | 10 |
| 14 | 60 | 70 | 80 | 100 | 100 | 100 | 0 |
| A | 0 | 100 | 30 | 80 | 90 | 80 | 30 |
| B | 20 | 0 | 0 | 0 | 10 | 0 | 0 |
| C | 25 | 10 | 0 | 90 | 40 | 35 | 0 |

EXAMPLE 6, WORKING EXAMPLE

Grape Juice Test 20 ml. of a nutrient solution of grape juice and distilled water in the ratio of 1:1 were filled into Petri dishes and mixed with the active materials set out in the following Table. The active material concentration amounted to 31 ppm. Subsequently, the experimental batches were each inoculated with 50 μl. of a Botrytis spore suspension, prepared by slurrying of the Botrytis spores from an agar culture with distilled water.

After a culturing period of 10 or 20 days at 20° C., the extent of the fungus development on the nutrient solution surface was assessed.

The degree of action was calculated in % according to the following formula:

$$100 - \frac{\text{fungal growth, treated}}{\text{fungal growth, untreated}} \times 100$$

TABLE 4

Effectiveness of the materials according to the invention and of comparative agents in % degrees at 31 ppm active material concentration after 10 or 20 days period of action

| active material No. | % effectiveness after 10 days | after 20 days |
|---|---|---|
| 1 | 100 | 100 |
| 3 | 100 | 100 |
| 4 | 100 | 100 |
| 5 | 100 | 85 |
| 6 | 100 | 90 |
| 7 | 100 | 100 |
| 8 | 100 | 100 |
| 9 | 100 | 100 |
| 11 | 100 | 90 |
| 12 | 100 | 100 |
| 13 | 100 | 100 |
| 14 | 100 | 100 |
| 15 | 100 | 100 |
| 16 | 100 | 100 |
| A | 100 | 100 |
| B | 95 | 70 |
| C | 60 | 20 |

Especially active materials according to the invention, such as e.g. active compound 16, still show 80% effectiveness after 20 days, even at 2 ppm.

EXAMPLE 7, WORKING EXAMPLE

Grape Juice With Resistant *Botrytis Cinerea* Strains

The method of working according to Example 6 was repeated with the difference that inoculation was with Botrytis spores of a Botrytis strain which showed resistance towards N-(3,6-dichlorophenyl)-substituted imides. The active material concentration amounted to 8 ppm. Whereas with active material 7, a 65% effectiveness was achieved against this strain, with comparison A at the same active material concentration only 20% effectiveness was to be ascertained. As additional comparison, there was used "Ronilan" (=3-(3,5-dichlorophenyl)-5-ethenyl-5-methyl-2,4-oxazolidinedione; Registered Trade Mark of BASF AG) which, against the same strain, only achieved 26% effectiveness even at 62 ppm active material concentration.

EXAMPLE 8: WORKING EXAMPLE

*Botrytis Cinerea* On Paprika (*Capsicum Annuum*)

Young paprika plants which have developed the first true pair of leaves are sprayed dripping wet with an aqueous solution of the active material formulation. After the drying of the spray coating, the plants are artificially infected with a suspension of Botrytis spores and thereafter kept at 95-98% atmospheric humidity and 20° C. in a climatic chamber. 6 days after the inoculation, the experiment is assessed. The degrees of attack are determined by comparison with untreated control plants, as well as with a comparison preparation.

TABLE 5

Effectiveness of active materials according to the invention and of comparison agents in % degrees at 500 ppm active material concentration on paprika plants

| active material No. | % effectiveness |
|---|---|
| 2 | 80 |
| 3 | 90 |
| 7 | 85 |
| 14 | 95 |
| A | 45 |
| B | 50 |
| C | 10 |

If one carries out the same experiment with Botrytis spores which, as in Example 7, show resistance phenomena against N-(3,5-dichlorophenyl) substituted imides, then the degree of effectiveness decreases, for example, with comparison substance A to about one half of the value with sensitive strains whereas, for example, with active material 7, practically the same effectiveness was obtained against sensitive as well as against resistant strains.

EXAMPLE 9: WORKING EXAMPLE

Effectiveness against *Puccinia Triticina* (Wheat Brown Rust)

Young wheat plants in the 2-leaf stage were sprayed dripping wet with an aqueous active material suspension. After the drying of the active material coating, the plants were infected by spraying with an aqueous uredospore suspension. After 24 hours standing in a dark moist chamber, the plants were placed in a greenhouse at 20° to 22° C. and 65 to 75% rel. atmospheric humidity. After 10 to 14 days incubation time, the percentages of the degrees of attack were determined by comparison of the attacked leaf surfaces with untreated, infected control plants.

TABLE 6

Effectiveness of the compounds according to the invention and of comparison agents in % degrees at 500 ppm active material concentration

| active material No. or comparison | % effectiveness |
|---|---|
| 1 | 90 |
| 7 | 90 |
| 14 | 70 |
| 15 | 80 |
| 16 | 100 |
| A | 0 |
| B | 65 |
| C | 60 |

Against bean rust (*Uromyces phaseoli*), quite similar combating values are mostly achieved as against wheat brown rust.

EXAMPLE 10: WORKING EXAMPLE

Effectiveness Against *Pythium Ultimum* In The Case Of Soil Application

The active material was mixed uniformly in a concentration of 500 ppm in soil which was artificially infected with *Pythium ultimum*. The so treated soil was placed into plastic pots (in each case 4 repetitions per test substance) and each sown with 10 pea seeds. These pots were kept for 10 days at 24° to 26° C. and at an atmospheric humidity of 75 to 90%. Thereafter, the number of healthy, germinated plants was determined. The degree of action was calculated by comparison with infected but untreated soil samples. The results are summarised in the following Table.

TABLE 7

Effectiveness of active materials according to the invention and of comparison agents in % degrees at 500 ppm active material concentration against *Pythium ultimum*

| active material No. | % effectiveness |
|---|---|
| 1 | 100 |
| 7 | 100 |
| 8 | 100 |
| 11 | 75 |
| 12 | 75 |
| 16 | 80 |
| A | 25 |
| B | 0 |
| C | 45 |

We claim:
1. Compounds of the formula

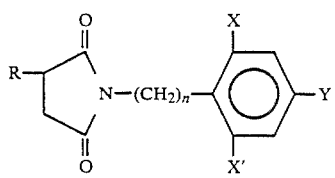

wherein R signifies a chlorine, bromine or iodine atom, n represents 0, 1, 2 or 3, X, X¹ and Z each represents the same or different substituents, namely, hydrogen atoms, fluorine atoms or methyl groups, and Y is a hydrogen, fluorine, chlorine or bromine atom or a methyl group, with a proviso that when n is 0 and R is simultaneously chlorine, at least one of the residues X, X¹, Y and Z is not a hydrogen atom and that when Z does not signify a hydrogen atom, at least one of the residues X, X¹ and Y also does not signify a hydrogen atom.

2. Compounds of the formulae

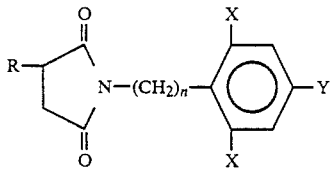

and

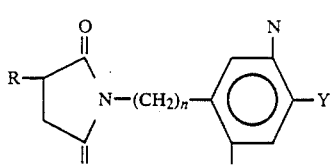

wherein R signifies a chlorine, bromine or iodine atom, n represents 0, 1, 2 or 3, each X represents the same or different substituents, namely, hydrogen atoms, fluorine atoms or methyl groups, and Y is a hydrogen, fluorine, chlorine or bromine atom or a methyl group, whereby each of X and Y are the same with the proviso that when n is 0 and R is simultaneously chlorine, at least one of X, Y and Z is not a hydrogen atom and that when Z does not signify a hydrogen atom, at least one of X and Y also does not signify a hydrogen atom and L and N are the same or different substituents, namely, methyl groups or flourine atoms and M signifies a hydrogen atom or a methyl group.

3. A compound as defined in claim 2 corresponding to the formula

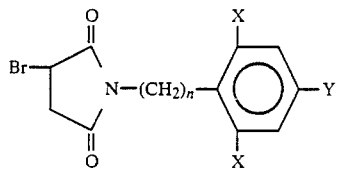

wherein n represents 0, 1, 2 or 3; each X represents the same substituents, namely, hydrogen atoms, fluorine atoms or methyl groups, and Y is a hydrogen, fluorine, chlorine or bromine atom or a methyl group.

4. A method for killing and controlling fungi which attack plants or plant products which comprises applying to the fungi or its living area an amount of a composition effective to kill and/or control said fungi, said composition comprising, as the fungicidal-active material, a compound of the formula

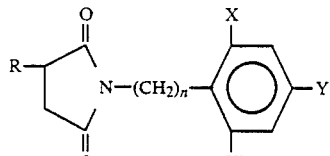

wherein R signifies a chlorine, bromine or iodine atom, n represents 0, 1, 2 or 3, X, X¹ and Z each represents the same or different substituents, namely, hydrogen atoms, fluorine atoms or methyl groups, and Y is a hydrogen, fluorine, chlorine or bromine atom or a methyl group, with the proviso that when n is 0 and R is simultaneously chlorine, at least one of the residues X, X¹, Y and Z is not a hydrogen atom and that when Z does not signify a hydrogen atom, at least one of the residues X, X¹ and Y also does not signify a hydrogen atom.

5. Compounds of the formula

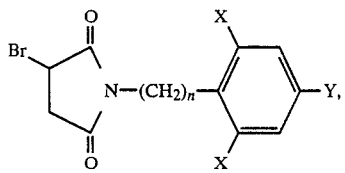
(IV)

wherein n, X and Y have the meanings given for formula (I), whereby the residues X are each the same residues.

6. Compound of the formula

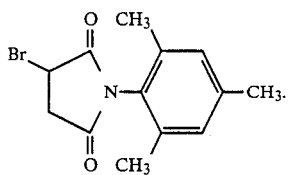
(V)

7. Process for the preparation of compounds of the formula

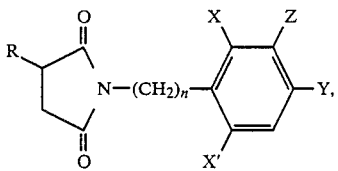
(I)

wherein R, n, X, X', Y and Z have the meanings given in claim 1, characterised in that compounds of the formula

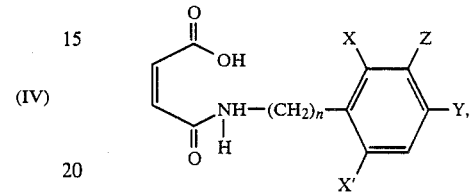
(IX)

are reacted with those of the formula

CH₃COR' whereby, R, n, X, X', Y and Z have the meanings given in claim 1 and R' signifies a chlorine or bromine atom, and, if R in formula (I) signifies an iodine atom, the so obtained product of the formula

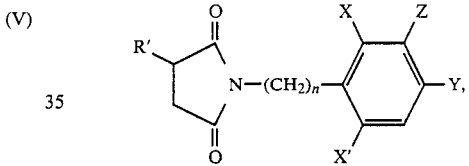
(XI)

is subsequently reacted with alkali metal iodide in per se known manner.

* * * * *